(12) United States Patent
Flagle et al.

(10) Patent No.: US 8,057,432 B2
(45) Date of Patent: Nov. 15, 2011

(54) SELECTIVE LOCKING MECHANISM FOR AN INTRODUCER DEVICE

(75) Inventors: Jacob Flagle, Indianapolis, IN (US); Zachary R. Nicoson, Indianapolis, IN (US); Joseph L. Mark, Indianapolis, IN (US); Terry D. Hardin, Irvine, CA (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 636 days.

(21) Appl. No.: 12/125,655

(22) Filed: May 22, 2008

(65) Prior Publication Data

US 2009/0292244 A1 Nov. 26, 2009

(51) Int. Cl.
*A61M 5/00* (2006.01)

(52) U.S. Cl. ........................................ 604/116

(58) Field of Classification Search .................. 604/116; 606/130
See application file for complete search history.

(56) References Cited

U.S. PATENT DOCUMENTS

| | | | | |
|---|---|---|---|---|
| 4,798,212 A * | 1/1989 | Arana | ............................. | 600/562 |
| 4,943,986 A * | 7/1990 | Barbarisi | ........................... | 378/37 |
| 4,981,142 A * | 1/1991 | Dachman | ....................... | 600/562 |
| 5,056,523 A * | 10/1991 | Hotchkiss et al. | .............. | 600/427 |
| 5,590,653 A * | 1/1997 | Aida et al. | ..................... | 600/411 |
| 5,681,327 A * | 10/1997 | Heywang-Koebrunner | . | 606/130 |
| 5,702,405 A * | 12/1997 | Heywang-Koebrunner | . | 606/130 |
| 5,957,935 A * | 9/1999 | Brown et al. | .................. | 606/130 |
| 6,206,832 B1 * | 3/2001 | Downey et al. | ................ | 600/439 |
| 6,508,786 B2 * | 1/2003 | Huitema et al. | ................ | 604/116 |
| 6,846,315 B2 * | 1/2005 | Barzell et al. | .................. | 606/130 |
| 7,235,084 B2 * | 6/2007 | Skakoon et al. | ............... | 606/130 |
| 7,379,769 B2 * | 5/2008 | Piron et al. | ..................... | 600/415 |
| 7,438,692 B2 * | 10/2008 | Tsonton et al. | ................ | 600/564 |
| 7,507,210 B2 * | 3/2009 | Hibner et al. | .................. | 600/567 |
| 7,815,651 B2 * | 10/2010 | Skakoon et al. | ............... | 606/130 |
| 7,828,744 B2 * | 11/2010 | Rioux et al. | .................... | 600/562 |
| 2002/0038117 A1 * | 3/2002 | Tokita et al. | ...................... | 606/1 |
| 2007/0118034 A1 * | 5/2007 | Mark | ............................. | 600/431 |
| 2007/0233157 A1 * | 10/2007 | Mark et al. | .................... | 606/130 |
| 2009/0292244 A1 * | 11/2009 | Flagle et al. | ................... | 604/116 |

* cited by examiner

*Primary Examiner* — Nicholas D Lucchesi
*Assistant Examiner* — Diva Ranade
(74) *Attorney, Agent, or Firm* — Rader, Fishman & Grauer, PLLC (57) ABSTRACT

A selectively lockable introducer assembly is disclosed that comprises an introducer cannula and a needle guide. The introducer cannula is defined by a proximal end and a distal end and includes a lumen extending therebetween. The needle guide is defined by a body portion that includes at least one channel extending therethrough. The introducer cannula is configured to be selectively receivable within the at least one channel and the introducer cannula may be selectively lockable with respect to the needle guide such that the introducer cannula is selectively prevented from moving laterally with respect to the needle guide.

22 Claims, 10 Drawing Sheets

SELECTIVE LOCKING MECHANISM FOR AN INTRODUCER DEVICE

TECHNICAL FIELD

The present disclosure relates generally to needle guides used for biopsy systems, and in particular to a needle guide configured for guiding an introducer device into a patient.

BACKGROUND

During certain biopsy procedures, a needle guide may be used through which a portion of an introducer cannula passes. The needle guide serves to minimize non-axial movement or deflection of the introducer during a biopsy to ensure that the introducer is inserted into the correct location of a patient's tissue adjacent a target lesion.

In breast biopsy procedures, for example, an MRI biopsy procedure, needle guides are often used in connection with a compression plate. The compression plate may include a plurality of grid-like openings. Prior to the start of the breast biopsy procedure, the compression plate is pressed against the breast, thereby compressing it, and a needle guide is inserted into one of the grid-like openings where the lesion to be biopsied may be found. The needle guide includes at least one channel extending therethrough. The channel is used through which a portion of an introducer passes. A biopsy needle is then inserted into the introducer.

As the biopsy is being taken, the introducer may unintentionally move in the direction of the z-axis. That is, the introducer cannula may advance further into the breast than intended, or, alternatively, the introducer may partially pull out from the breast as well. One known device for securing the introducer in place is a retaining ring located around an outer diameter of the introducer. The ring includes an outer diameter that is greater than an inner diameter of the channel. Therefore, the introducer is unable to advance further into the breast. However, the ring is unable to restrain the introducer in the opposite direction, away from the breast, and therefore the introducer is still able to partially pull out from the breast.

Accordingly, there exists a need for a device that will secure the introducer such that the introducer is unable to pull out from the breast as the biopsy is being taken.

SUMMARY

A selectively lockable introducer assembly is disclosed that comprises an introducer cannula and a needle guide. The introducer cannula is defined by a proximal end and a distal end and includes a lumen extending therebetween. The needle guide is defined by a body portion that includes at least one channel extending therethrough. The introducer cannula is configured to be selectively receivable within the at least one channel and the introducer cannula may be selectively lockable with respect to the needle guide such that the introducer cannula is selectively prevented from moving laterally with respect to the needle guide.

DETAILED DESCRIPTION

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

According to various exemplary illustrations described herein, a needle guide is provided that includes a body portion. The body portion is configurable between an uncompressed position and a compressed position. The body portion further includes at least one channel extending therethrough. At least one slot extends outwardly from the channel. The slot permits at least a portion of the body portion to compress inwardly between the uncompressed position and the compressed position. The channel includes a first diameter and a second diameter, the first diameter defined by the uncompressed position and the second diameter defined by the uncompressed position. The first diameter is greater than the second diameter.

Figure 1:
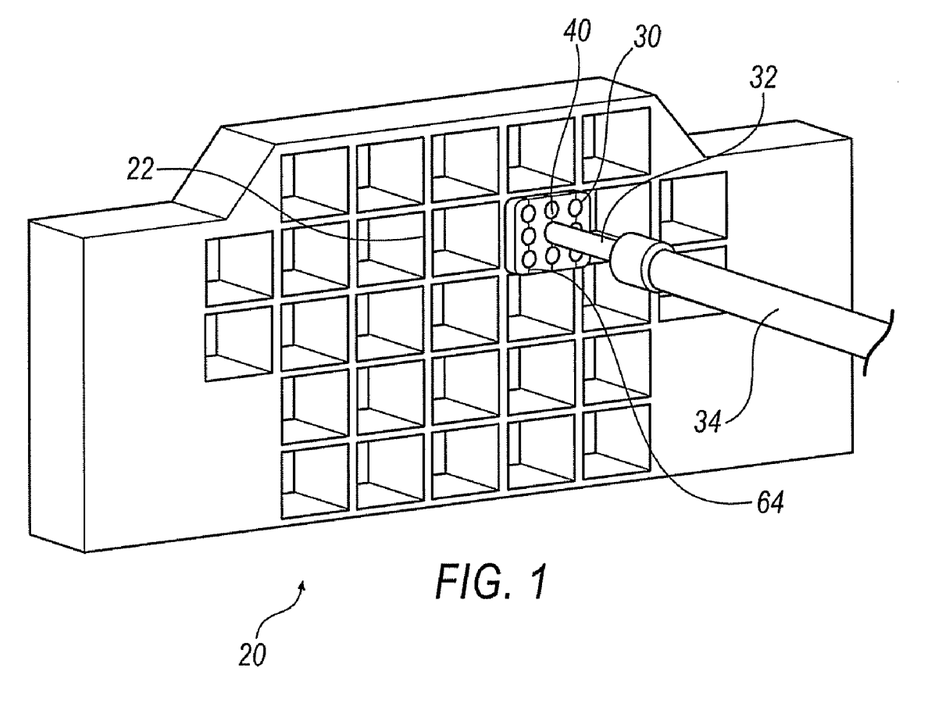
FIG. 1 is an elevational perspective view of a compression plate, a needle guide, and an introducer with a stylet inserted therein.

Turning now to the drawings and in particular to FIG. 1, an exemplary compression plate 20 is shown, including a plurality of grid-like openings 22. In the illustration of FIG. 1, the compression plate 20 is used with a needle guide 30. Prior to the start of a biopsy procedure, the compression plate 20 is pressed against a body area of interest. In a breast biopsy procedure, for example, the compression plate is pressed against the breast, thereby compressing the breast. An introducer 32 with a stylet is inserted into one of the openings 40 of the needle guide 30 where the lesion to be biopsied may be found. The needle guide 30 includes a series of slots 64 that allow for the needle guide 30 to compress inwardly such that the introducer 32 is unable to move inwardly and outwardly from the opening 40 when locked, as discussed in greater detail below.

Figure 2A:
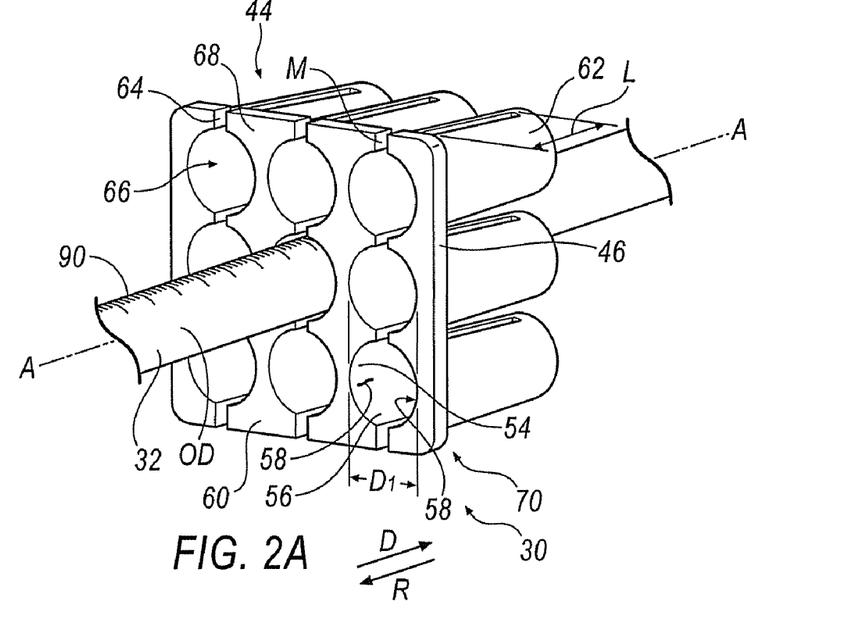
FIG. 2A is an elevational perspective view of the needle guide and a portion of the introducer in a first uncompressed position.
Figure 2B:
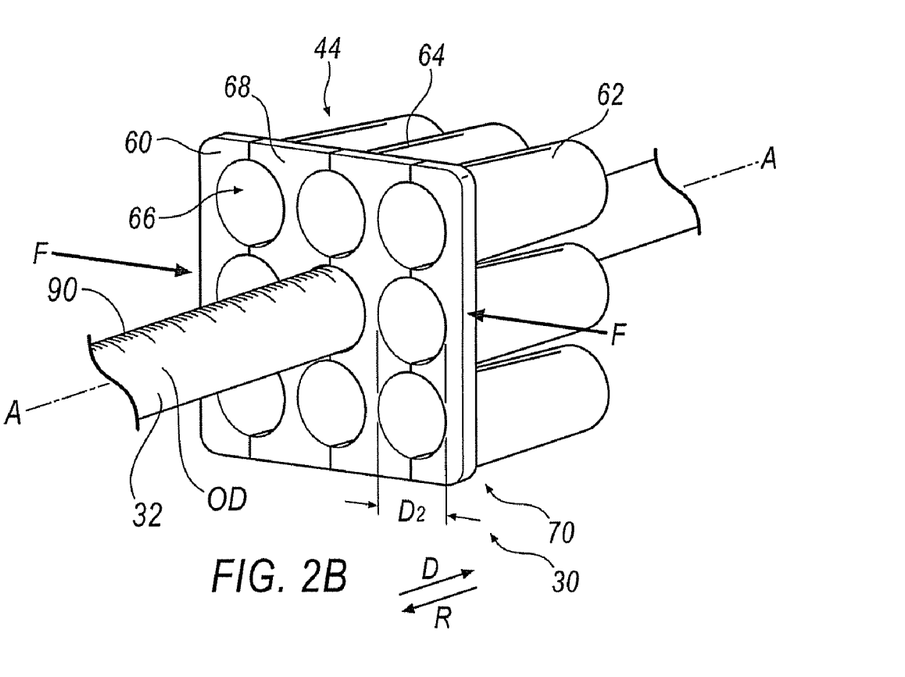
FIG. 2B is an elevational perspective view of the needle guide and the introducer of FIG. 2A in a second compressed position.

FIG. 2A is an illustration of the needle guide 30 and the introducer 32 in a first, uncompressed position. The needle guide 30 includes a body portion 44, an outer periphery 46, and a proximate face 60. The needle guide also includes at least one channel 62 extending therethrough. Although FIGS. 2A-2B illustrate the needle guide 30 including nine channels 62, it should be noted that any number of channels 62 may be used.

The series of slots 64 are located along the proximate face 60 of the needle guide 30. The slots 64 extend outwardly from each of the channels 62, and towards either of the outer periphery 46 or an adjacent channel 62, depending on the placement of the slots 64. That is, if the slot 64 is located adjacent the outer periphery 46, then the slot 64 extends from the channel 62 to the outer periphery 46. If the slot 64 is adjacent to another channel 62, then the slot 64 extends from one of the channels 62 towards another channel 62. In the illustration as shown, the slots 64 are each located along a middle section M of each of the channels 62, however the slots 64 may be located along any point of the channels 62.

As illustrated in FIG. 2A, the slots 64 extend along a length L of the body portion 44. The length L is parallel with an axis A-A of the needle guide 30. The slots 64 permit at least a portion of the body portion 44 to compress inwardly between the uncompressed position and a compressed position, which is discussed in greater detail below. In the embodiment shown, each of the channels 62 include two generally opposing slots 64, with one of the slots 64 located along an upper portion 54 of the channel 62 and the other slot 64 located along a bottom portion 56 of the channel 62. Although FIG. 2A illustrates the channels 62 having two generally opposing slots 64 along the upper portion 54 and the bottom portion 56, the slots 64 may also be located at other positions, such as, for example, along opposing sides 58 of the channel 62 as well.

In the uncompressed position, the needle guide 30 is loosely engaged with the introducer 32. More specifically, when the needle guide 30 is in the uncompressed position, an inner surface 66 of the channel 62 is unable to closely engage with an outer diameter OD of the introducer 32. As seen in FIG. 2A, the channel 62 includes a first unlocked diameter D1. The unlocked diameter D1 is greater than the outer diameter OD of the introducer 32. Thus, when in the uncompressed position, the introducer 32 is able to freely move in a direction D towards the needle guide 30 as well as in a direction R that is away from the needle guide 30.

However, as the needle guide 30 is inserted into one of the openings 22 of the compression plate 20, a compressive force F is exerted along the outer periphery 46 of the needle guide 30. That is, when the compressive force F is exerted along the outer periphery 46, the needle guide 30 is urged inwardly from the first uncompressed position (FIG. 2A) into the second compressed position (FIG. 2B). Because the needle guide 30 can be selectively compressed inwardly by the compressive force F when in the uncompressed position, the needle guide 30 is unlocked.

FIG. 2B illustrates the needle guide 30 in the compressed position, after the compressive force F has been applied. For clarity, the compression plate 20 has been omitted. The body portion 44 of the needle guide 30 is urged inwardly by the compressive force F when placed inside the opening 22 of the compression plate 20 (not shown in FIG. 2B). In the compressed position, the slots 64 are urged together. In one embodiment, the slots 64 are urged together such that the slots 64 close and the needle guide 30 is unable to compress further inwardly. The needle guide 30 is also unable to expand outwardly because the outer periphery 46 is restrained by the opening 22 of the compression plate 20. Thus, the needle guide 30 is effectively locked in the compressed position.

When the needle guide 30 is in the compressed position, as in FIG. 2B, the channel 62 is defined by a second diameter D2. The second diameter D2 is less than the first diameter D1. Moreover, the second diameter D2 is about equal to or slightly less then the outer diameter OD of the introducer 32. Therefore, when in the compressed position, the outer diameter OD of the introducer 32 is closely engaged with the inner surface 66 of the channel 62. Thus, when in the compressed position, the introducer 32 is unable to move inwardly in the direction D and outwardly in the direction R from the channel 62.

Figure 2C:
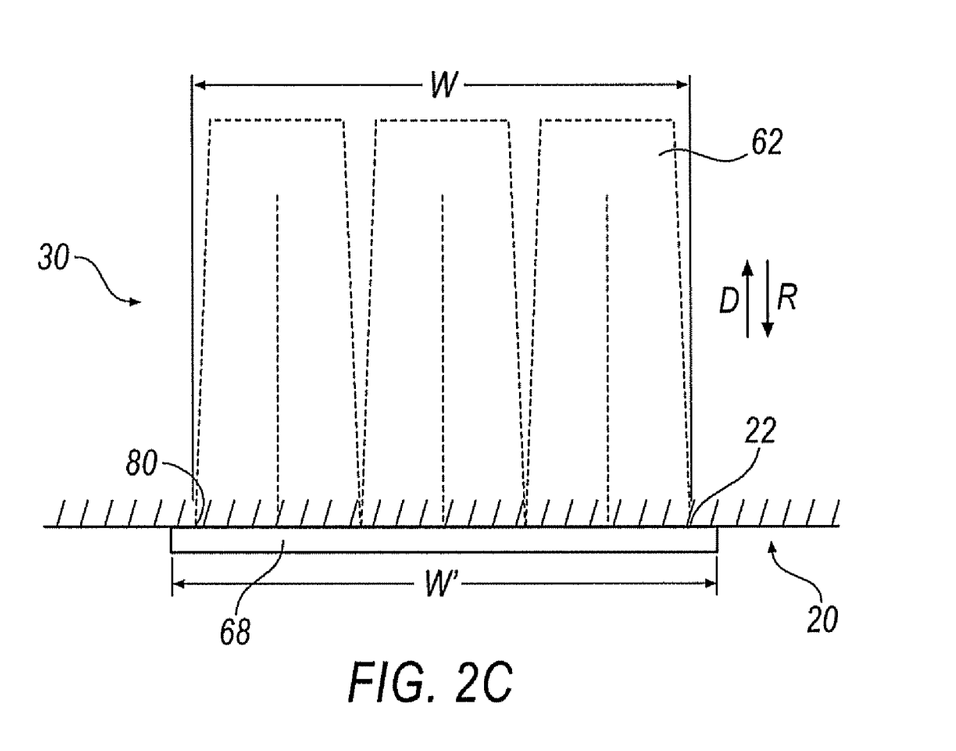
FIG. 2C is a partially sectioned plan view of the needle guide and the portion of the compression plate.

In the illustrations as shown in FIGS. 2A-2B, the body portion 44 includes an optional support member 68. The support member 68 is connected to the body portion 44 at a proximate end 70 of the body portion 44. The support member 68 includes the proximate face 60. In one illustration as seen in FIG. 2C, the support member 68 includes a width W' that is greater than a width W of the opening 22 of the compression plate 20. Thus, when inserted into the compression plate 20, the needle guide 30 is seated such that a back surface 80 of the support member 68 is flush with the opening 22. The back surface 80 of the support member 68 retains the needle guide 30 within the opening 22 of the compression plate 20 such that the needle guide 30 is unable to advance further into the opening 22, and in the direction D. Including the support member 68 may also provide a grip that the user can easily hold on to when a user removes the needle guide 30 from the opening 22.

When the introducer 32 is slid into the channel 62 the needle guide 30 is in the uncompressed position. Then, once the introducer 32 is positioned to the desired depth, the needle guide 30 is placed within one of the openings 22 of the compression plate 20. As seen in FIGS. 2A-2B, the introducer 32 may also include a series of graduated markings 90 that indicate the depth of the introducer 32 within a breast.

When placed within the opening 22, the needle guide 30 compresses from the uncompressed position (FIG. 2A) to the compressed position (FIG. 2B). This is because the compressive force F urges the needle guide 30 to move inwardly from the uncompressed position to the compressed position. As discussed in greater detail below, the needle guide 30 may also include a snapping movement between the compressed and uncompressed configuration, therefore providing a tactile feedback to a user. The tactile feedback allows the user to know when the needle guide 30 is in the locked versus the unlocked position.

In one example of the needle guide 30, the slot 64 snaps between the uncompressed position and the compressed position. More specifically, the slot 64 only has two positions, a first open position as seen in FIG. 2A, and a second closed position as seen in FIG. 2B. Thus, when the needle guide 30 is pushed into the opening 22 of the compression plate 20, the slots 64 will snap shut with an abrupt movement. A sharp sound may also be used to indicate to a user that the needle guide 30 is in the locked position within the compression plate 20.

Figure 3A:
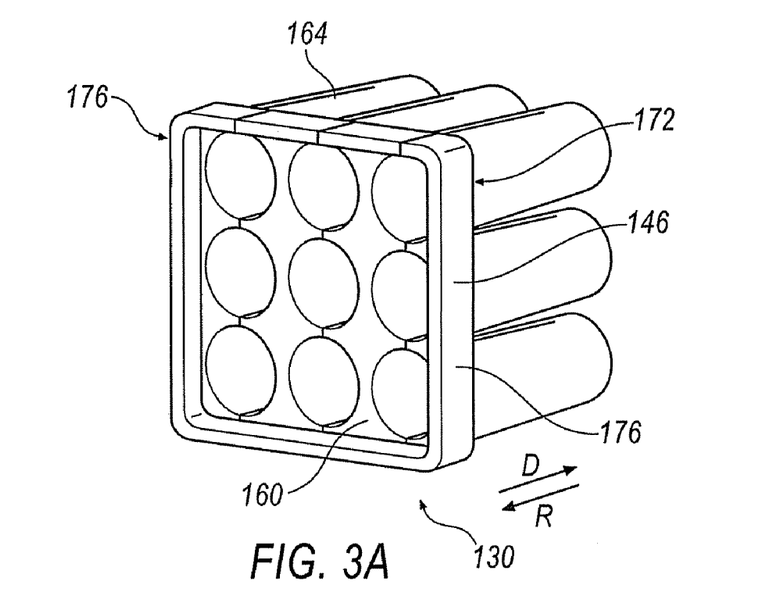
FIG. 3A is an elevational perspective view of an alternative illustration of the needle guide including a flange.
Figure 3B:
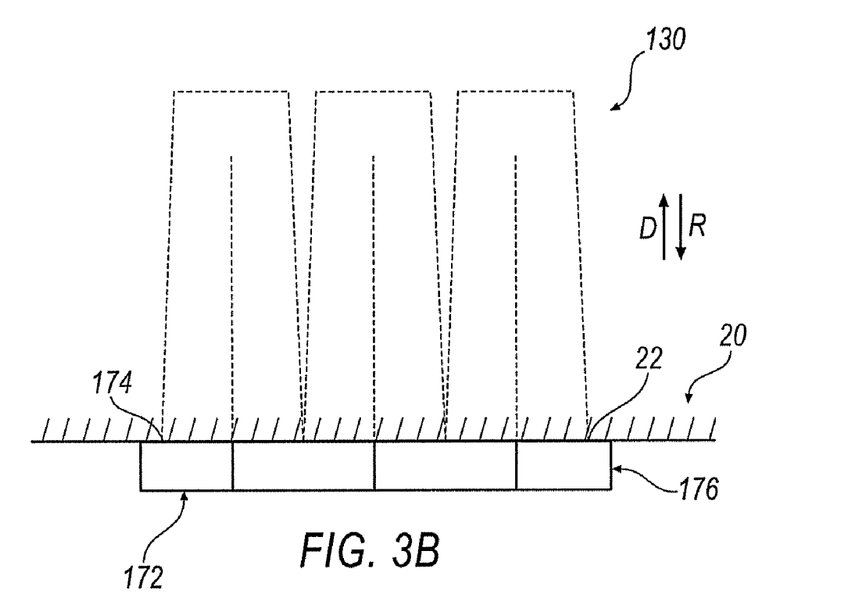
FIG. 3B is a partially sectioned plan view of the needle guide in FIG. 3A and a portion of the compression plate.

FIGS. 3A-3B are alternative embodiments of a needle guide 130 where the proximate face 160 includes a flange 172 located along at least a portion of the outer periphery 146. The flange 172 extends outwardly from the proximate face 160, in the direction R. The flange 172 provides a grip such that when the needle guide 130 is placed within the opening 22 of the compression plate 20, a user will have a surface along the needle guide 130 that is easy to grasp.

As best seen in FIG. 3B, the flange 172 protrudes from the opening 22 of the compression plate 20. A back surface 174 of the flange 172 is in contact with the compression plate 20, and the outer periphery 176 of the flange 172 is slightly larger than the opening 22. Therefore, when inserted within the opening 22, the needle guide 30 is unable to travel past the back surface 174, and the needle guide 30 is unable to advance further into the opening 22 in the direction D. The flange 172 provides a handle that a user may hold on to when the needle guide 130 is removed from the opening 22 of the compression plate 20.

Figure 4A:
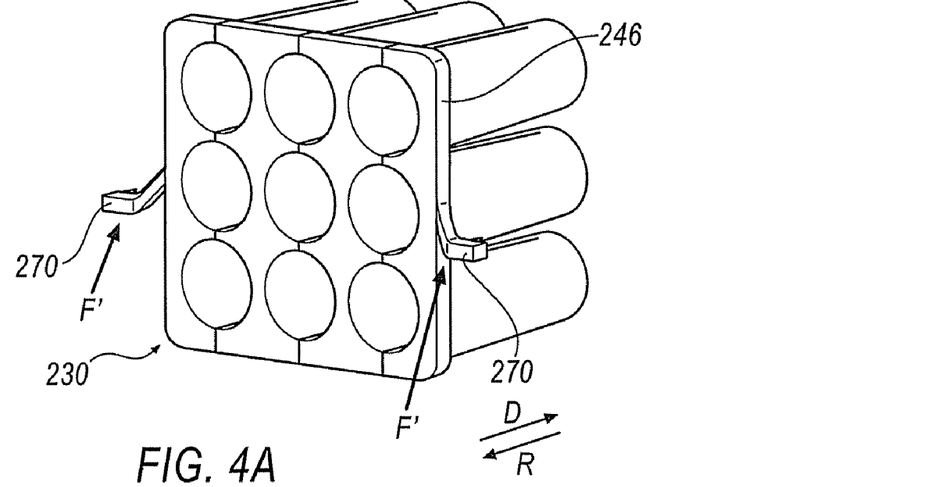
FIG. 4A is an elevational perspective view of another alternative illustration of the needle guide including a pair of outwardly extending arms.
Figure 4B:
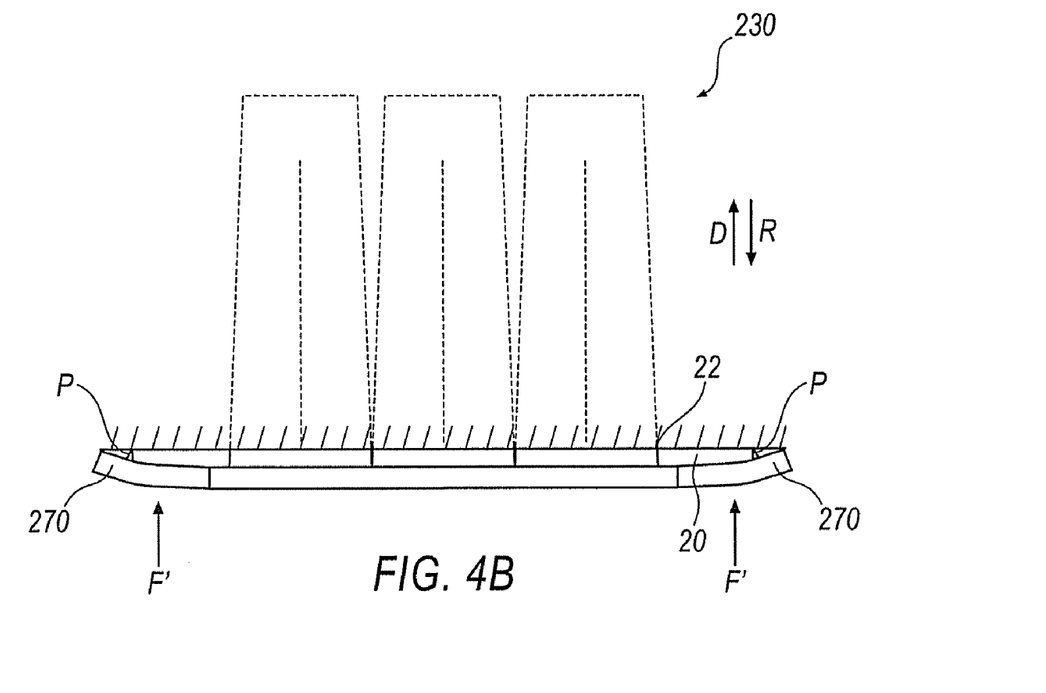
FIG. 4B is a partially sectioned plan view of the needle guide in FIG. 4A with a force being acted on the arms, and a portion of the compression plate.

In yet another alterative illustration of a needle guide 230, as seen in FIGS. 4A-4B, a pair of outwardly extending arms 270 are included that extend from opposing sides of the outer periphery 246. A pivot member P is mounted to a portion of each arm 270. When the arms 270 are pushed by an inwards force F' towards the needle guide 230 and in the direction D, the pivot member P contacts a portion of the compression plate 20 and needle guide 230 is urged into the uncompressed configuration and unlocks. That is, as seen in FIG. 4B, when the inward force F' is exerted upon the arms 270, the pivot member P cooperates with arms 270 such that needle guide 230 is pushed outwardly and away from the opening 22 of the compression plate 20 and in the direction R. Thus, the arms 270 and pivot member P facilitate removal of the needle guide 230 from the opening 22 of the compression plate 20 by a user.

Figure 5A:
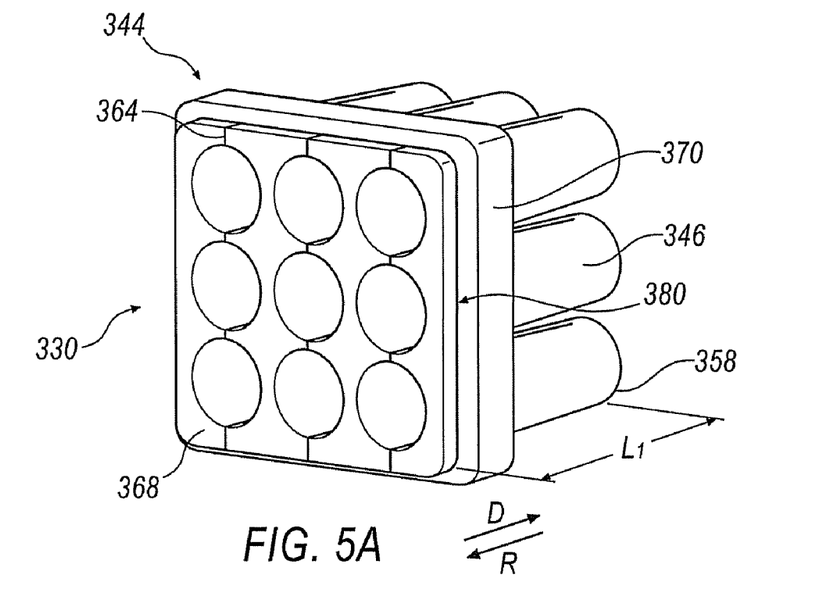
FIG. 5A is an elevational perspective view of yet another alternative illustration of the needle guide including a moveable ring.

Yet another alternative illustration of a needle guide 330 is shown in FIG. 5A. The needle guide 330 includes a moveable ring 370 that encircles the outer periphery 346. The ring 370 is moveable along a length L' that is measured from the back surface 380 of the support member 368 towards a distal end 358 of the body portion 344 of the needle guide 330. In the illustration as shown, the ring 370 is placed behind the support member 368. The support member 368 retains the ring 370 along the outer periphery 346 of the needle guide 330. The ring 370 urges the needle guide 330 into the compressed configuration. More specifically, when the moveable ring 370 is advanced to the proximate face 360 of the needle guide 330, the slots 364 are urged together, thereby compressing the needle guide 330 into the compressed and locked configuration.

Figure 5B:
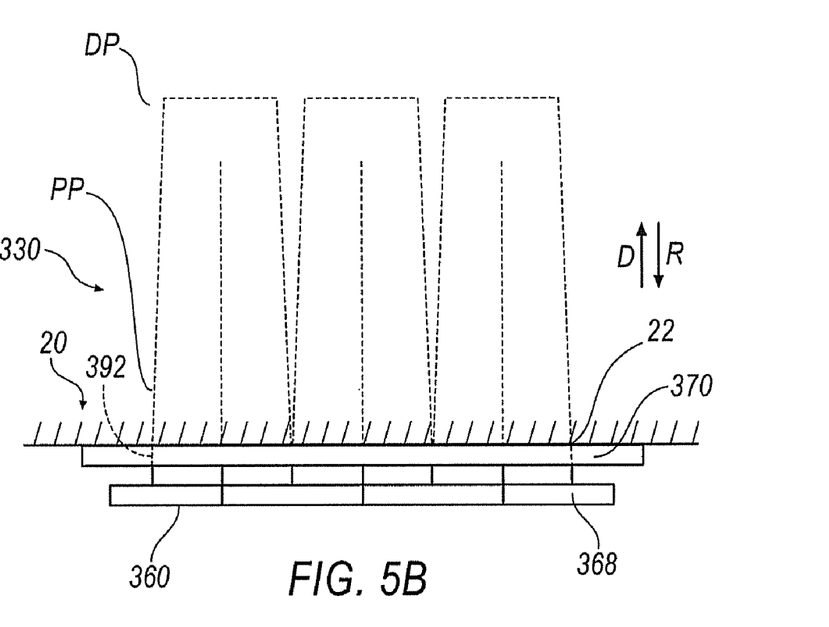
FIG. 5B is a partially sectioned plan view of the needle guide in FIG. 5A and a portion of the compression plate.
Figure 6:
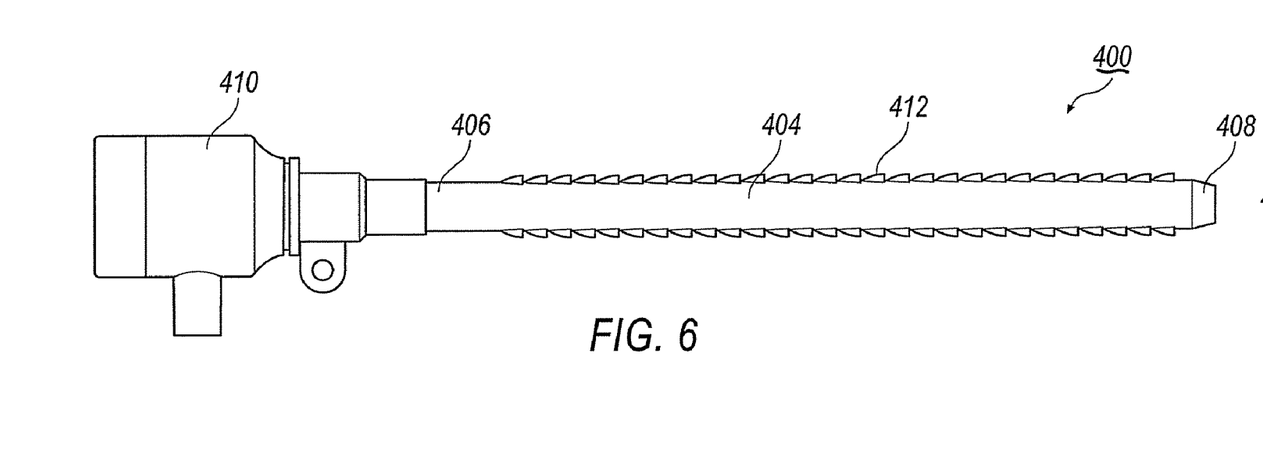
FIG. 6 is an elevational view of an embodiment of an introducer assembly.

FIG. 5B illustrates a needle guide 330 inserted into an opening 22 of the compression plate 20. The needle guide 330 is tapered inwardly, and includes a distal end outer periphery DP and a proximate end outer periphery PP. The distal end outer periphery DP is less than the proximate end outer periphery PP. The moveable ring 370 includes an inner diameter 392 that is smaller than the proximate end outer periphery PP but greater than the distal end outer periphery DP.

The needle guide 330 is urged inwardly and into the compressed position when the ring 370 is advanced towards the proximate face 360 of the needle guide 330 in the direction R. That is, the inner diameter 392 of the ring 370 compresses the needle guide 330 inwardly, and urges the slots 364 together. When the ring 370 is retracted away from the proximate face 360, and pushed in the direction D, the needle guide 330 will unlock into the uncompressed position.

FIGS. 6-9 illustrate an arrangement of a selectively lockable introducer assembly 400 that cooperates with a needle guide 402 to maintain a desired position for introducer assembly 400. Introducer assembly 400, best seen in FIGS. 6 and 7, includes a generally hollow introducer cannula 404 defined by a proximal end 406 and a distal end 408. An introducer hub 410 may be secured to proximal end 406 of introducer cannula 404. Introducer hub 410 includes an opening therethrough that is in communication with an inner lumen 411 extending through introducer cannula 404 and may also include a haemostatic valve (not shown).

Figure 7:
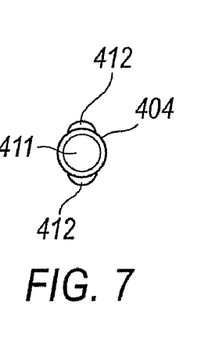
FIG. 7 is an end view of the introducer assembly of FIG. 6.

Positioned on an outer portion of introducer cannula 404 is a plurality of retaining members 412. Retaining members 412 extend upwardly from an outer surface of introducer cannula 404. In one arrangement, retaining members 412 are positioned along a substantial portion of the length of introducer cannula 404. In another arrangement, retaining members 412 are also positioned so as to be spaced at equi-distance intervals. In another arrangement, two sets of retaining members 412 are positioned on introducer cannula 404, with the sets being positioned 180° apart from one another, as seen in FIG. 7. Retaining members 412 will be explained in further detail below.

Figure 8:
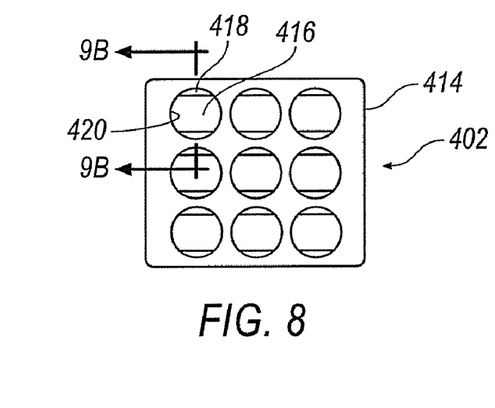
FIG. 8 is a plan view of an embodiment of a needle guide.

Referring now to FIG. 8, needle guide 402 will be described. Needle guide 402 includes a body portion defined by an outer periphery 414 and at least one channel 416 extending therethrough. Although FIG. 8 illustrates the needle guide 402 including nine channels 416, it should be noted that any number of channels 416 may be used.

Disposed within each channel 416 is at least one retaining tang 418 positioned on an internal surface 420 of each channel 416. Retaining tangs 418 are positioned so as to extend inwardly into each channel 416, and away from inside surface 420 of each channel 416. In one arrangement, a plurality of retaining tangs 418 extend along the length of inside surface 420 of each channel 416. In another arrangement, there are at least a pair of retaining tangs 418, with each retaining tang 418 being positioned 180° apart from one another, as shown in FIG. 8. In one arrangement, retaining tangs 418 are formed so as to have a complimentary shape to retaining members 412, to be explained below.

Figure 9A:
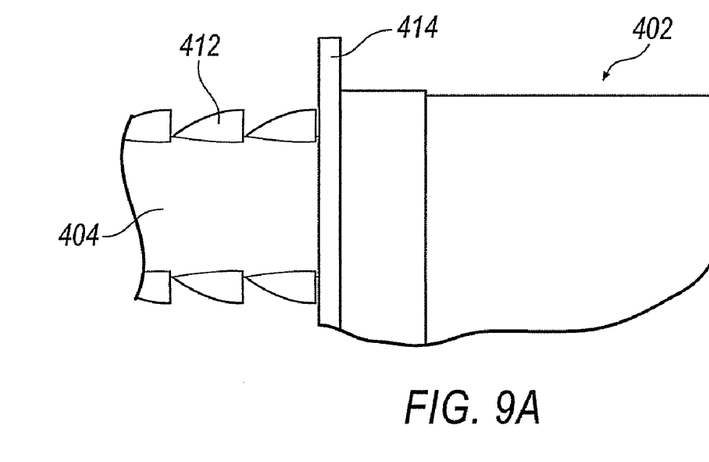
FIG. 9A is an enlarged a side elevational view of a portion of the introducer assembly of FIG. 6, disposed in an engaged configuration within the needle guide of FIG. 8.
Figure 9B:
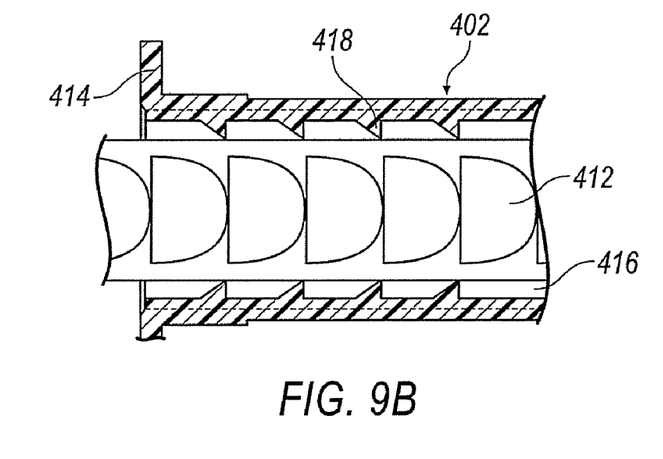
FIG. 9B is an enlarged and partial cross-sectional view of the introducer assembly of FIG. 6, in a disengaged configuration within the needle guide of FIG. 8.

Turning now of FIGS. 9A-9B, the interaction between introducer cannula 404 and needle guide 402 will now be explained. Once a site of interest for performing a biopsy or treatment has been determined, and needle guide 402 has been appropriately positioned with a compression plate 20 (see FIG. 1), introducer cannula 404 is inserted into a desired channel 416. In one exemplary arrangement, to permit introducer cannula 404 to enter needle guide 402, introducer cannula 404 is appropriately rotated such that retaining members 412 are positioned approximately 90° from retaining tangs 418. In this configuration, introducer cannula 404 may freely slide within channel 416 to a desired depth. To assist with ascertaining the appropriate depth, the outer surface of introducer cannula 404 may be provided with markings or other indicia to indicate depth.

After a desired depth for insertion of introducer cannula 404 has been reached, introducer cannula 404 may be selectively locked into position by rotating introducer cannula 404 within channel 416 by approximately 90.° Once rotated, retaining members 412 engage with retaining tangs 418 in a complementary manner. More specifically, retaining members 412 are rotated so as to place a retaining tang 418 between adjacent retaining members 412. Once so engaged, introducer cannula 404 is locked into position with needle guide 402 in the x, y, and z axes. Such locking action prevents accidental dislodgement of introducer cannula 404 during a surgical or therapeutic procedure, including accidental sliding of introducer cannula 404 along the z axis. Thus, a stable pathway to a site of interest is maintained. Once a procedure is complete, introducer cannula 404 may be disengaged from needle guide 402 by simply rotating introducer cannula 404 sufficiently such that retaining members 412 become disengaged with retaining tangs 418 and introducer cannula 404 may be slid out of needle guide 402.

Figure 10:
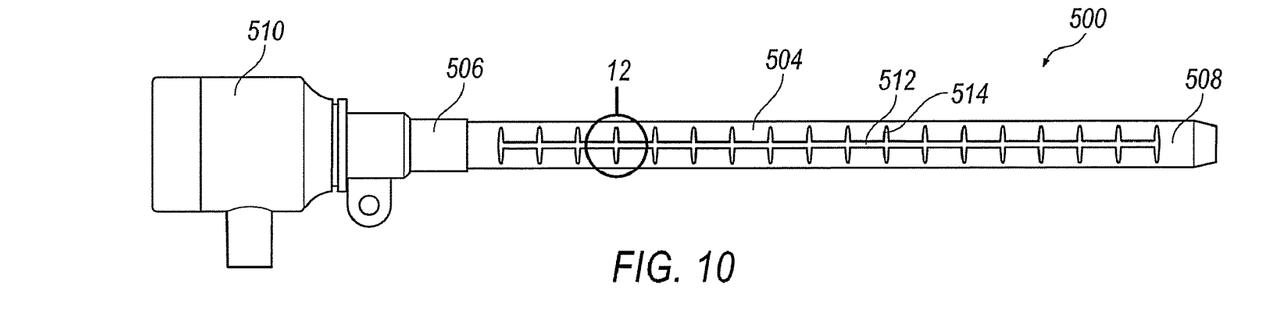
FIG. 10 is an elevational view of another embodiment of an introducer assembly.
Figure 11:
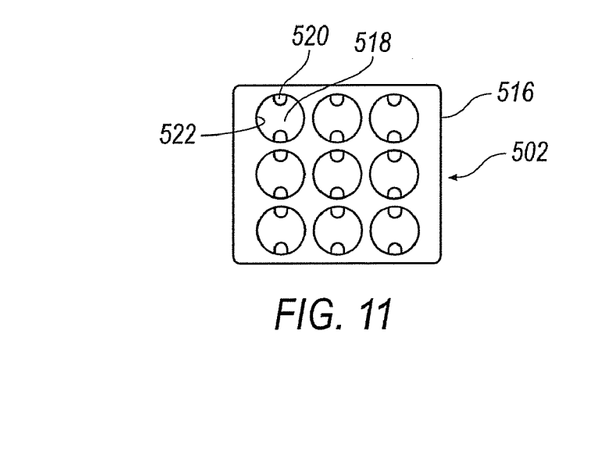
FIG. 11 is a plan view of an embodiment of a needle guide.
Figure 12:
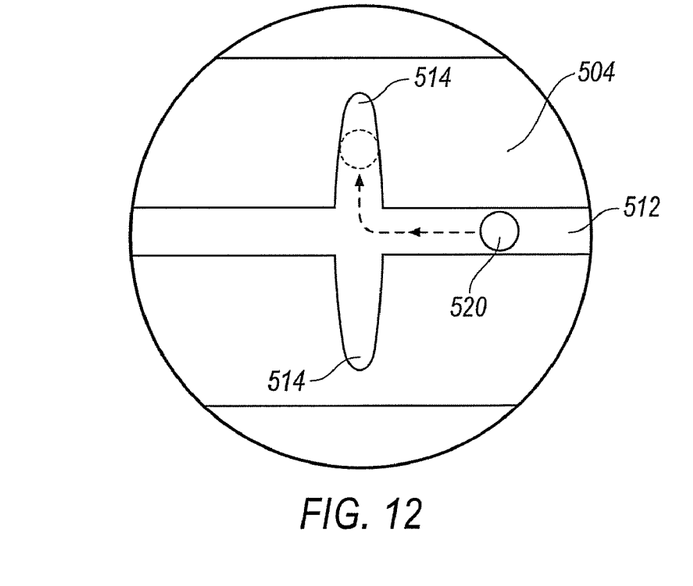
FIG. 12 is an enlarged side elevational view of an encircled area 12 of the introducer assembly of FIG. 10, with the introducer assembly disposed in an engaged configuration within the needle guide of FIG. 11.

Referring to FIGS. 10-12, another arrangement of a selectively lockable introducer assembly 500 is shown. Similar to the arrangement shown in FIGS. 6-9, introducer assembly 500 cooperates with a needle guide 502 to maintain a desired position for introducer assembly 500. Introducer assembly 500, best seen in FIG. 10, includes a generally hollow introducer cannula 504 defined by a proximal end 506 and a distal end 508. An introducer hub 510 may be secured to the proximal end 506 of introducer cannula 504. Introducer hub 510 includes an opening therethrough that is in communication with an inner lumen extending through introducer cannula 504. Introducer hub 510 may also include a haemostatic valve (not shown) to minimize blood flow.

Positioned on an outer portion of introducer cannula 504 is at least one central groove 512. In one arrangement, a central groove 512 extends along a substantial portion of the length of introducer cannula 504. Extending away from central groove 512 is a plurality of spaced apart engagement grooves 514 that extend radially along the outer surface of introducer cannula 504. In one arrangement, engagement grooves 514 are spaced apart at equi-distance intervals and are arranged in pairs disposed on either side of central groove 512, as shown in FIG. 10. In another arrangement, a second central groove may be formed on the outside surface of introducer cannula 504, approximately 180° from the first central groove 512. Like the first central groove 512, the second central groove also includes a plurality of engagement grooves. Engagement grooves 514 will be explained in further detail below.

Referring now to FIG. 11, needle guide 502 will be described. Needle guide 502 includes a body portion defined by an outer periphery 516 and at least one channel 518 extending therethrough. Although FIG. 11 illustrates the needle guide 502 as having nine channels 518, it should be noted that any number of channels 518 may be used.

Disposed within each channel 518 is at least one retaining tang 520 positioned on an internal surface 522 of each channel 518. Retaining tangs 520 are positioned so as to extend inwardly into each channel 518, and away from inside surface 522 of each channel 518. In one arrangement, a plurality of retaining tangs 520 may be provided that extend along the length of inside surface 522 of each channel 518. In another arrangement, there are at least a pair of retaining tangs 520, with each retaining tang being positioned 180° apart from one another, as shown in FIG. 11.

Turning now to FIG. 12, the interaction between introducer cannula 504 and needle guide 502 will now be explained. Once a site of interest for performing a biopsy or treatment has been determined, and needle guide 502 has been appropriately positioned within compression plate 20, introducer cannula 504 is inserted into a desired channel 518. To permit introducer cannula 504 to enter needle guide 502, introducer cannula 504 is rotated such that central groove 512 is aligned with retaining tang 520. Retaining tang 520 is appropriately sized to enter central groove 512 such that introducer cannula 504 may freely slide within channel 518 to a desired depth. To assist with ascertaining the appropriate depth, the outer surface of introducer cannula 504 may be provided with markings or indicia to indicate the depth. After a desired depth of introducer cannula 504 has been reached, introducer cannula 504 may be locked into position by slightly rotating introducer cannula 504. The rotation of introducer cannula 504 causes an engagement groove 514 to slide over retaining tang 520 (shown in phantom in FIG. 12). Once retaining tang 520 has been captured in engagement groove 514, introducer cannula 504 is locked into position within needle guide 502 such that introducer cannula is effectively prohibited from being displaced during a surgical or other therapeutic procedure.

Once a procedure is complete, introducer cannula 504 may be easily disengaged from needle guide 502. For example, introducer cannula 504 is rotated in such a manner so as to place retaining tang 520 in central groove 512. Once in central groove 512, introducer cannula 504 may be slid out of needle guide 502.

Figure 13:
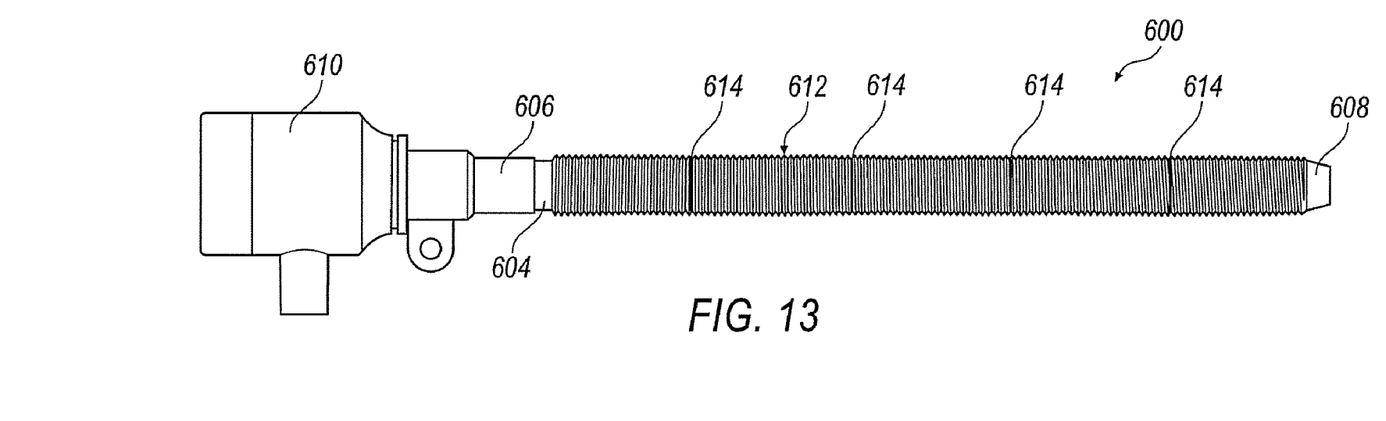
FIG. 13 is an elevational view of another embodiment of an introducer assembly.
Figure 14:
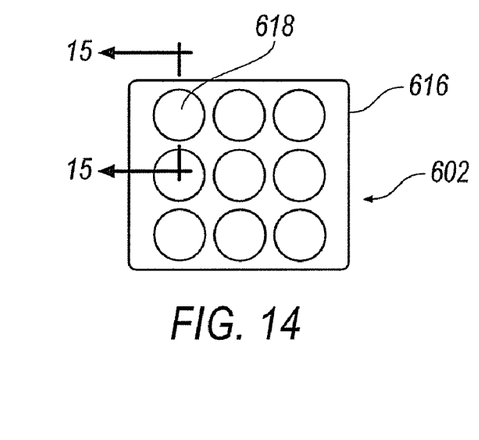
FIG. 14 is plan view of an embodiment of a needle guide.
Figure 15:
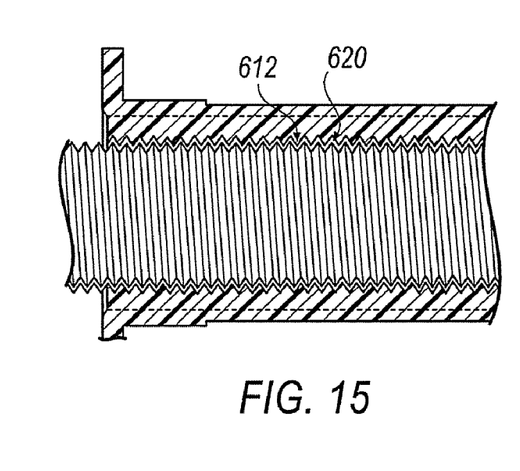
FIG. 15 is an enlarged and partial cross-sectional view of the introducer assembly of FIG. 13, with the introducer assembly disposed in an engaged configuration within the needle guide of FIG. 14.

Referring to FIGS. 13-15, another arrangement of a selectively lockable introducer assembly 600 is shown. Introducer assembly 600 cooperates with a needle guide 602 to maintain a desired position, in the x, y, and z axes, for introducer assembly 600. Introducer assembly 600, best seen in FIG. 13, includes a generally hollow introducer cannula 604 defined by a proximal end 606 and a distal end 608. An introducer hub 610 may be secured to proximal end 606 of introducer cannula 604. Introducer hub 610 includes an opening therethrough that is in communication with an inner lumen extending through introducer cannula 604, and may also include a haemostatic valve (not shown) to control blood flow from the body.

Outer surface of introducer cannula 604 is threaded 612 along at least a portion of its length. In one arrangement, outer surface of introducer cannula 604 is threaded along a substantial portion of introducer cannula 604. In one arrangement, spaced along threads 612 at predetermined intervals are depth indicators 614, such as indicia or markings. Use of depth indicators 614 will be explained in further detail below.

Referring now to FIG. 14, needle guide 602 will be described. Needle guide 602 includes a body portion defined by an outer periphery 616 and at least one channel 618 extending therethrough. Although FIG. 14 illustrates the needle guide 602 including nine channels 618, it should be noted that any number of channels 618 may be used. Each channel 618 is threaded 620 (see FIG. 15) so as to cooperate with threads 612 of introducer cannula 604 (to be explained below).

Referring now of FIG. 15, the interaction between introducer cannula 604 and needle guide 602 will now be explained. Once a site of interest for performing a biopsy or treatment has been determined, and needle guide 602 has been appropriately positioned within compression plate 20, introducer cannula 604 is directed into a desired channel 618. Introducer cannula 604 is then rotated in a first direction into the desired channel 618, such that threads 612 of introducer cannula 604 engage with threads 620 of channel 618. After a desired depth of introducer cannula 604 has been reached, which may be visually indicated by depth indicators 614, rotation of introducer cannula 604 is stopped. However, due to the interaction of threads 612 and 620, introducer cannula 604 is effectively prevented from being displaced during a surgical or other therapeutic procedure.

Once a procedure is complete, introducer cannula 604 may be easily disengaged from needle guide 602 simply by rotating introducer cannula 604 in a second direction so as to disengage threads 612 and 620 from one another until introducer cannula 604 is free of needle guide 502.

While the present disclosure has been particularly shown and described with reference to the foregoing preferred embodiments, it should be understood by those skilled in the art that various alternatives to the embodiments of the disclosure described herein may be employed in practicing the disclosure without departing from the spirit and scope of the disclosure as defined in the following claims. It is intended that the following claims define the scope of the disclosure embodiments within the scope of these claims and their equivalents be covered thereby. This description of the disclosure should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. A selectively lockable needle guide, comprising:
a body portion, wherein the body portion includes at least one channel extending therethrough and one or more slots operably connected to the at least one channel, wherein the slots cooperate with the channels such that the body portion is selectively configurable between an uncompressed configuration wherein at least the portion of the channel adjacent the slot is defined by a first diameter, and a compressed configuration, wherein at least the portion of the channel adjacent the slot is defined by a second diameter that is smaller than the first diameter;
wherein the body portion is configured such that as the body portion is moved into the compressed configuration, the slot cooperates with the channel to reconfigure the body portion into the compressed configuration so as to prevent an instrument that is inserted within the channel from moving laterally with respect to the needle guide.

2. The selectively lockable needle guide of claim 1, wherein the slot extends to an outer periphery of the body portion.

3. The selectively lockable needle guide of claim 2, wherein the slot extends between two channels.

4. The selectively lockable needle guide of claim 1, further comprising a flange extending outwardly from a proximate face of the needle guide and located along at least a portion of an outer periphery of the body portion, wherein the flange is sized to have a periphery that is larger than the size of a periphery of the body portion.

5. The selectively lockable needle guide of claim 1, further including a moveable ring encircling an outer periphery of the needle guide, the ring urging the body portion inwardly and into the compressed position when the ring is advanced towards a distal end portion of the body portion.

6. The selectively lockable needle guide of claim 1, wherein the body portion includes a support member, the support member is connected to a proximal face of the body portion.

7. The selectively lockable needle guide of claim 6, wherein the support member includes at least one outwardly extending arm including a pivot member, the pivot member configured to selectively contact a portion of a compression grid into which the body portion is inserted, to force the body portion in a proximal direction and at least partially out of the compression grid.

8. The selectively lockable needle guide of claim 1, wherein the slot includes an uncompressed open position and a compressed closed position, the slot being inwardly compressible and snapping between the uncompressed open position and the compressed closed position.

9. The selectively lockable needle guide of claim 1, wherein each of the channels are tapered inwardly from a proximal end to a distal end of the body portion, such that a distal end of the body portion includes a distal periphery that is less than a periphery of the body portion at the proximal end.

10. A selectively lockable introducer assembly, comprising:
an introducer cannula defined by a proximal end and a distal end; and
a needle guide defined by a body portion, wherein the body portion includes at least one channel extending therethrough;
wherein the introducer cannula is configured to be selectively receivable within the at least one channel; and
wherein the introducer cannula further comprises a plurality of retaining members and wherein each channel of the needle guide further comprises at least one retaining tang extending from an inner surface of each channel; wherein the retaining members of the introducer cannula cooperate with the at least one retaining tang of the channel of the needle guide to selectively lock the introducer cannula to the needle guide to prevent the introducer cannula from moving laterally with respect to the needle guide.

11. The selectively lockable introducer assembly of claim 10, wherein the retaining members are positioned equi-distance apart along a portion of an outer surface of the introducer cannula.

12. The selectively lockable introducer assembly of claim 10, wherein the retaining members are arranged in two rows on an outer surface of the introducer cannula, the rows being positioned 180° apart.

13. The selectively lockable introducer assembly of claim 12, wherein each channel includes at least a pair of retaining tangs formed on an inside surface of each channel and extending inwardly into the channel, each of the retaining tangs being positioned 180° apart from one another.

14. The selectively lockable introducer assembly of claim 10, further comprising a plurality of depth indicators positioned on an outer surface of the introducer cannula.

15. The selectively lockable introducer assembly of claim 10, wherein the introducer cannula further comprises at least one central channel formed on an outside surface of the introducer cannula and a plurality of retaining grooves extending away from the central channel; and
wherein the at least one retaining tang is sized to fit within the central groove and the retaining grooves.

16. The selectively lockable introducer assembly of claim 15, wherein the introducer cannula includes a pair of central grooves extending along the length of the introducer cannula, the central grooves being spaced apart by 180°.

17. The selectively lockable introducer assembly of claim 16, wherein each channel includes at least a pair of retaining tangs, each retaining tang being position 180° from one another.

18. The selectively lockable introducer assembly of claim 15, further comprising a plurality of pairs of retaining grooves extending from the central groove, each pair comprising a first retaining groove and a second retaining groove that are arranged along a common axis.

19. The selectively lockable introducer assembly of claim 15, further comprising a plurality of depth indicators positioned on an outer surface of the introducer cannula.

20. A selectively lockable introducer assembly, comprising:
   an introducer cannula defined by a proximal end and a distal end; and
   a needle guide defined by a body portion, wherein the body portion includes at least one channel extending therethrough;
   wherein the introducer cannula is configured to be selectively receivable within the at least one channel; and
   wherein an outer surface of the introducer cannula is threaded along an outside surface of at least a portion of the introducer cannula and wherein an inner surface of each channel of the needle guide is threaded.

21. The selectively lockable introducer assembly of claim 20, further comprising a plurality of depth indicators positioned on an outer surface of the introducer cannula.

22. The selectively lockable needle guide of claim 1, wherein the body portion is transferred from the uncompressed configuration into the compressed configuration by the application of a circumferential force.

* * * * *